(12) United States Patent
Coenen et al.

(10) Patent No.: US 9,533,483 B2
(45) Date of Patent: Jan. 3, 2017

(54) APPARATUS FOR AND METHOD OF SHAPING AND APPLYING A SEGMENT TO A MOVING WEB

(71) Applicant: Kimberly-Clark Worldwide, Inc., Neenah, WI (US)

(72) Inventors: Joseph Daniel Coenen, Kaukauna, WI (US); Caleb E. Ihrig, Oshkosh, WI (US); Joseph J. Sina, Appleton, WI (US); Gerald Sosalla, Appleton, WI (US); Charles Robert Sample, Green Bay, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 218 days.

(21) Appl. No.: 14/497,899

(22) Filed: Sep. 26, 2014

(65) Prior Publication Data
US 2016/0089870 A1   Mar. 31, 2016

(51) Int. Cl.
| | |
|---|---|
| *B29C 55/06* | (2006.01) |
| *B29C 55/16* | (2006.01) |
| *B32B 38/00* | (2006.01) |
| *B29C 63/00* | (2006.01) |
| *B29C 55/10* | (2006.01) |

(Continued)

(52) U.S. Cl.
CPC ........... *B32B 38/0012* (2013.01); *B29C 55/06* (2013.01); *B29C 55/10* (2013.01); *B29C 55/165* (2013.01); *B29C 63/0026* (2013.01); *B29C 63/0034* (2013.01); *B29C 66/47* (2013.01); *B29C 66/81465* (2013.01); *B32B 38/1866* (2013.01); *A61F 2013/15821* (2013.01); *B32B 37/144* (2013.01); *B32B 37/22* (2013.01); *B32B 38/0004* (2013.01); *B32B 38/1858* (2013.01); *B32B 2309/14* (2013.01); *B32B 2555/02* (2013.01)

(58) Field of Classification Search
None
See application file for complete search history.

(56) References Cited

U.S. PATENT DOCUMENTS

| | | |
|---|---|---|
| 4,578,133 A | 3/1986 | Oshefsky et al. |
| 4,650,532 A | 3/1987 | Kloehn et al. |

(Continued)

FOREIGN PATENT DOCUMENTS

| | | |
|---|---|---|
| WO | 9700654 A1 | 1/1997 |
| WO | 2009136822 A1 | 11/2009 |

OTHER PUBLICATIONS

International Search Report and Written Opinion of PCT/IB20105/057311, Jan. 11, 2016, 11 pages.

*Primary Examiner* — Barbara J Musser
(74) *Attorney, Agent, or Firm* — Armstong Teasdale LLP

(57) ABSTRACT

Apparatus for shaping a segment of material includes a forming member having a curved sidewall shaped complementary to a desired shape of the segment of material, and a conforming member having an applicator side and an engagement side disposed for engagement with the curved sidewall of the forming member. The conforming member includes a plurality of attachment regions disposed on the applicator side. Each attachment region is adapted to hold the segment of material on the conforming member. Engagement of the conforming member with the forming member causes the attachment regions to move from a first shape profile to a second shape profile, the second shape profile being the desired shape of the segment of material.

25 Claims, 10 Drawing Sheets

(51) Int. Cl.
  *B29C 65/00*   (2006.01)
  *A61F 13/15*   (2006.01)
  *B32B 37/14*   (2006.01)
  *B32B 37/22*   (2006.01)
  *B32B 38/18*   (2006.01)

(56) References Cited

U.S. PATENT DOCUMENTS

| | | |
|---|---|---|
| 4,675,016 A | 6/1987 | Meuli et al. |
| 4,726,873 A | 2/1988 | Ales et al. |
| 5,393,360 A | 2/1995 | Bridges et al. |
| 5,500,075 A | 3/1996 | Herrmann |
| 5,525,175 A | 6/1996 | Blenke et al. |
| 5,531,850 A | 7/1996 | Herrmann |
| 5,766,411 A | 6/1998 | Wilson |
| 6,440,246 B1 | 8/2002 | Vogt et al. |
| 6,540,857 B1 | 4/2003 | Coenen et al. |
| 8,168,034 B2 | 5/2012 | Otsubo |
| 8,685,197 B2 | 4/2014 | Yamamoto |
| 8,772,569 B2 | 7/2014 | Schneider et al. |
| 2002/0079040 A1 | 6/2002 | Quereshi et al. |
| 2002/0112950 A1 | 8/2002 | Topolkaraev et al. |
| 2002/0115977 A1 | 8/2002 | Topolkaraev et al. |
| 2003/0168155 A1 | 9/2003 | Popp et al. |
| 2003/0183325 A1 | 10/2003 | Popp et al. |
| 2003/0196253 A1 | 10/2003 | Rajala et al. |
| 2009/0149828 A1 | 6/2009 | Beckman et al. |

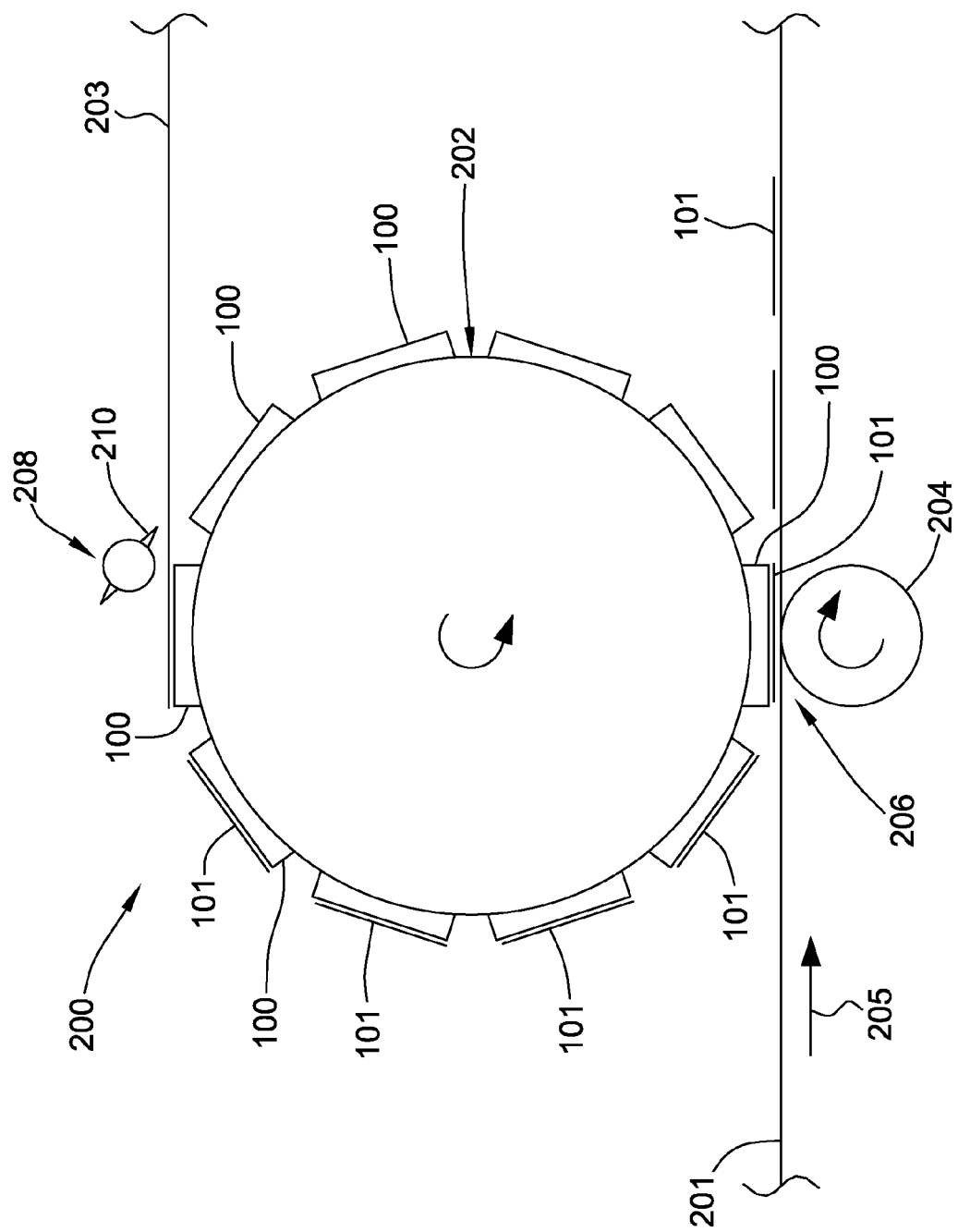

APPARATUS FOR AND METHOD OF SHAPING AND APPLYING A SEGMENT TO A MOVING WEB

FIELD

The field of the disclosure relates generally to apparatus for and methods of applying segments of material to a web, and more particularly to apparatus for and methods of shaping and applying segments of material to a moving web.

BACKGROUND

Absorbent garments, such as adult incontinence wear, infant and children's diapers, swim wear and training pants, include leg openings having an elastic portion around each leg opening, and a waist opening having an elastic portion at least partially surrounding the waist opening. The elastic portions about the leg openings are intended to fit snugly around a wearer's legs to inhibit leakage of body exudates from the garment. The leakage performance and aesthetic appearance of some absorbent articles can be improved by leg elastics having curvature and/or displacement (i.e., being profiled) along their lengths.

However, many known techniques for applying leg elastics to a moving web during the manufacture of absorbent articles are often limited in the amount of displacement (e.g., the amount of amplitude in a curved pattern) that can be achieved. Thus, leg elastics in most known absorbent articles produced at high line speeds are often straight or relatively straight. Some known techniques for placing leg elastics with significant amounts of displacement (i.e., curvature) onto a web at high line speeds have been unsatisfactory. For example, these techniques have resulted in leg elastics being placed off target.

Additionally, in at least some absorbent articles, more tension is desired in certain areas around the leg, such as in the crotch area, than in other areas around the leg, such as in the area away from the crotch. However, many known techniques for imparting a desired differential stretch profile to leg elastics have been unsatisfactory. For example, many known techniques are limited in the amount of differential stretch profile that can be imparted to a leg elastic.

Thus, there exists a need for an apparatus and method suitable for shaping segments of material in highly shaped profiles, imparting a desired stretch profile to such segments, and applying such segments to a moving web (e.g., a web moving at high line speeds).

SUMMARY

In one aspect, apparatus for shaping a segment of material generally comprises a forming member having a curved sidewall shaped complementary to a desired shape of the segment of material, and a conforming member having an applicator side and an engagement side disposed for engagement with the curved sidewall of the forming member. The conforming member includes a plurality of attachment regions disposed on the applicator side. Each attachment region is adapted to hold the segment of material on the conforming member. Engagement of the conforming member with the forming member causes the attachment regions to move from a first shape profile to a second shape profile, the second shape profile being the desired shape of the segment of material.

In another aspect, apparatus for applying a segment of material to a web generally comprises a rotating device and a shaping device connected to the rotating device. The shaping device includes a forming member having a curved sidewall shaped complementary to a desired shape of the segment of material, and a conforming member having an applicator side and an engagement side disposed for engagement with the curved sidewall of the forming member. The conforming member includes a plurality of attachment regions disposed on the applicator side. Each attachment region is adapted to hold the segment of material on the conforming member. Engagement of the conforming member with the forming member causes the attachment regions to move from a first shape profile to a second shape profile, the second shape profile being the desired shape of the segment of material.

In yet another aspect, a method of applying a segment of material to a web generally comprises guiding the segment of material to a conforming member having an engagement side and an applicator side having a plurality of attachment regions, holding the segment of material on the conforming member with the attachment regions, shaping the segment of material by engaging the conforming member with a forming member along the engagement side of the conforming member to move the attachment regions from a first shape profile to a second shape profile, and attaching the segment of material to the web.

BRIEF DESCRIPTION OF THE DRAWINGS

FIG. 11 schematically illustrates a portion of a manufacturing process for manufacturing the absorbent article of FIGS. 1 and 2, and an apparatus for shaping and applying segments of material to a moving web, the apparatus including a plurality of the shaping devices of FIG. 3.

DETAILED DESCRIPTION OF THE DRAWINGS

Figure 1:
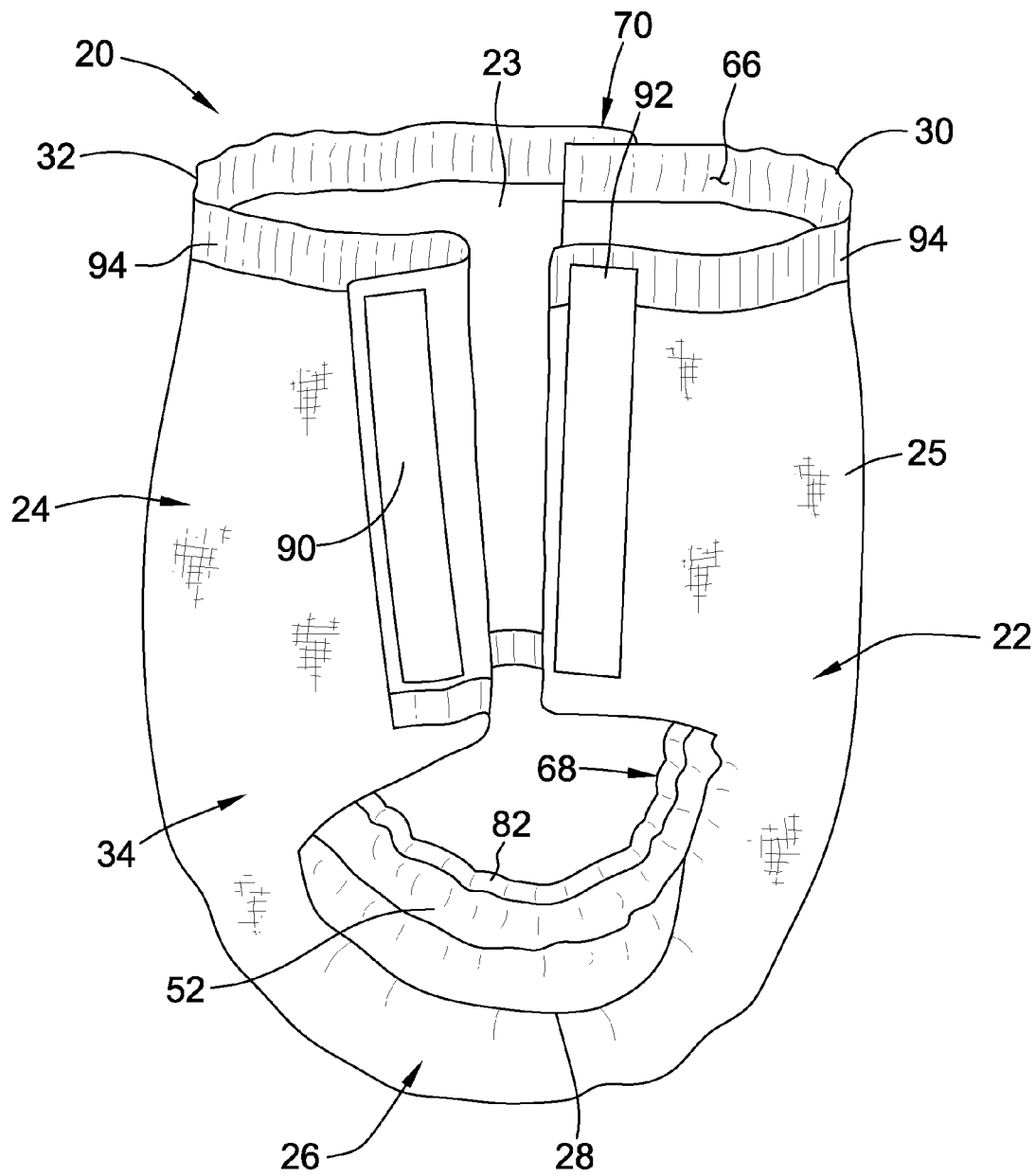
FIG. 1 is a side perspective of one suitable embodiment of an absorbent article shown in the form of a training pant, the training pant having a pair of refastenable side seams with one of the side seams being illustrated in a fastened configuration and the other side seam being illustrated in an unfastened configuration.
Figure 2:
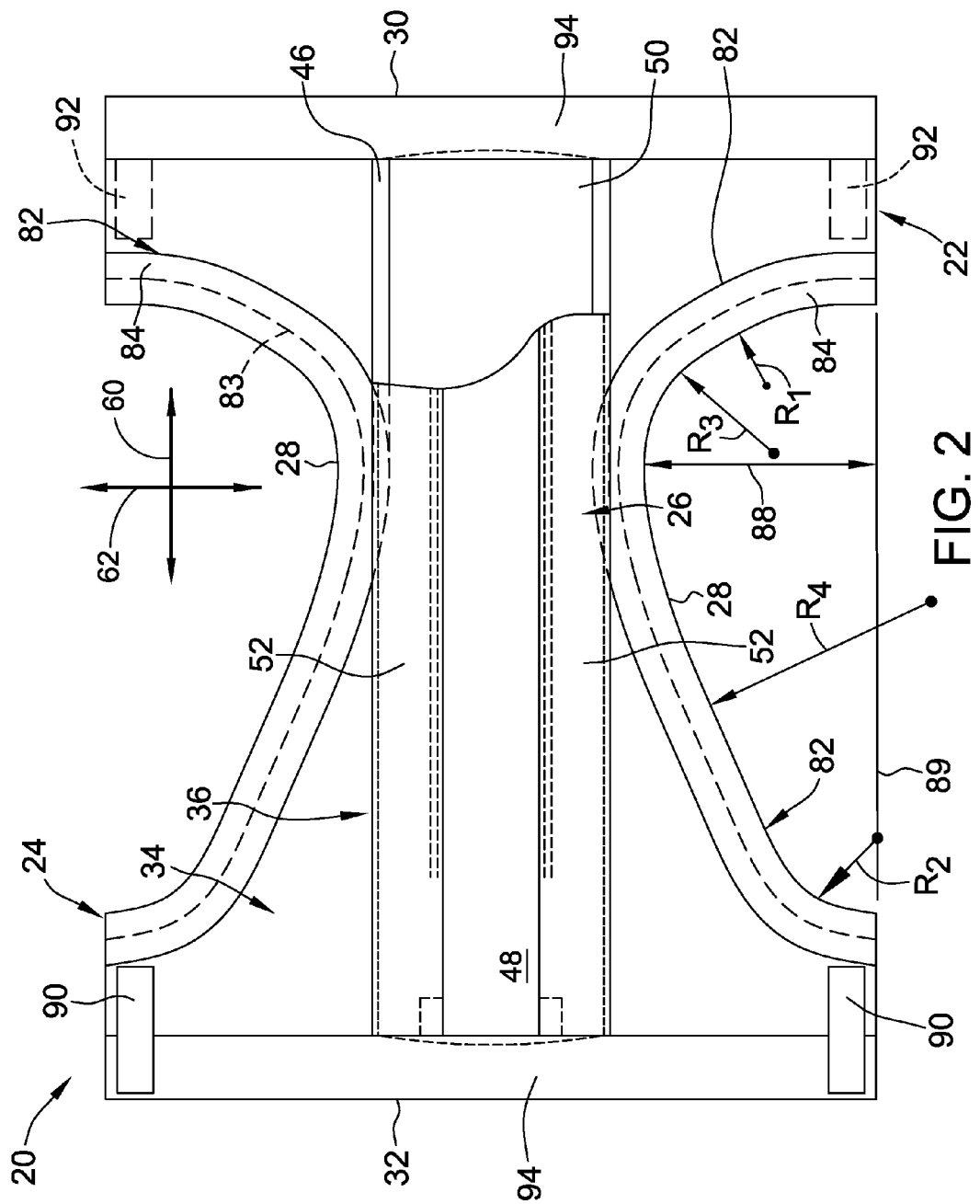
FIG. 2 is a top plan view of the absorbent article of FIG. 1 with the training pant in an unfastened, unfolded and laid flat condition, showing a surface of the training pant adapted to face the wearer during use with portions of the training pant being cut away to show underlying structures.

Referring now to the drawings and in particular to FIGS. 1 and 2, one suitable embodiment of an absorbent article is illustrated in the form of a child's toilet training pant and is indicated generally by the reference numeral 20. While the present disclosure will be made in the context of the training pant 20, it should be understood that aspects of the present disclosure are applicable to other absorbent articles, such as, for example, refastenable diapers, adult incontinence garments, diaper pants, swim diapers, feminine care articles and the like.

In one suitable embodiment, the training pant 20 is a disposable absorbent article. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. It is understood that in other suitable embodiments, the training pant 20 (or more broadly, the absorbent article) can be reusable. That is, the absorbent article can be intended for multiple uses without departing from some aspects of this disclosure.

The training pant 20 seen in FIGS. 1 and 2 has a front waist region 22, a back waist region 24, and a crotch region 26 disposed longitudinally between and interconnecting the front and back waist regions. The training pant 20 also has a pair of laterally opposite side edges 28 and a pair of longitudinally opposite waist edges, respectively designated front waist edge 30 and back waist edge 32. In the illustrated embodiment, the side edges 28 are arcuately shaped to provide the training pant 20 with a more body conforming shape. The front waist region 22 is contiguous with the front waist edge 30, and the back waist region 24 is contiguous with the back waist edge 32. As seen in FIG. 2, the training pant 20 defines a longitudinal direction 60 and a transverse direction 62 perpendicular to the longitudinal direction.

In the illustrated embodiment, the training pant 20 includes a body-facing side 23 (i.e., the side of the training pant 20 that faces the body of a wearer when worn) and a garment-facing side 25 (i.e., the side of the training pant 20 that faces away from the body of a wearer when worn). The training pant 20 also includes a chassis, indicated generally at 34, and an absorbent assembly, indicated generally at 36, attached to the chassis 34. The illustrated absorbent assembly 36 extends longitudinally from the front waist region 22 through the crotch region 26 to the back waist region 24.

The chassis 34 may comprise a variety of suitable materials including, for example and without limitation, a liquid permeable material that provides a generally cloth-like texture. The chassis 34 can be a single layer of material, or a multi-layered laminate structure. In other suitable embodiments, it is contemplated that the chassis 34 can be liquid impermeable. It is further contemplated that the chassis 34 can be vapor impermeable or vapor permeable (i.e., "breathable"). One suitable "breathable" material is composed of a microporous polymer film or a nonwoven fabric that has been coated or otherwise treated to impart a desired level of liquid impermeability.

It is also contemplated that the chassis 34 may be stretchable, and more suitably elastic. In particular, the chassis 34 is suitably stretchable and more suitably elastic in at least the transverse, or circumferential direction of the pant 20. In other embodiments, the chassis 34 may be stretchable, and more suitably elastic, in both the transverse and the longitudinal direction. It is contemplated that the chassis 34 can be stretchable in any suitable direction.

The absorbent assembly 36 of the illustrated embodiment is attached to the chassis 34 along at least the crotch region 26 of the training pant 20 using suitable attachment means including, but not limited to, adhesives, ultrasonic bonds, thermal bonds, pressure bonds, and combinations thereof.

As seen in FIG. 2, the absorbent assembly 36 comprises a liquid impermeable backsheet 46 and a bodyside liner 48 attached to the backsheet in a superposed relation by suitable means including, but not limited to, adhesives, ultrasonic bonds, pressure bonds, thermal bonds, and combinations thereof. An absorbent structure 50 is disposed between the backsheet 46 and the bodyside liner 48. The absorbent assembly 36 also includes a pair of containment flaps 52 for inhibiting the lateral flow of body exudates.

Suitably, the backsheet 46 prevents waste material from wetting articles, such as bed sheets and clothing, as well as the wearer and caregiver. The backsheet may comprise a variety of suitable materials including, for example and without limitation, a material which is substantially liquid impermeable. The backsheet 46 can be a single layer of liquid impermeable material, or may comprise a multi-layered laminate structure in which at least one of the layers is liquid impermeable. The backsheet 46 may also comprise a liquid permeable material, or the backsheet 46 may be omitted from the absorbent assembly 36 altogether. In such embodiments, the chassis 34 suitably comprises a liquid impermeable material to provide a liquid barrier to body exudates.

The backsheet 46 may also be stretchable, and more suitably elastic. In particular, the backsheet 46 is suitably stretchable and more suitably elastic in at least the transverse, or circumferential direction of the pant 20. The backsheet 46 may also be stretchable, and more suitably elastic, in both the transverse and the longitudinal direction.

The bodyside liner 48 is suitably compliant, soft-feeling, and non-irritating to the wearer's skin. The bodyside liner 48 is also sufficiently liquid permeable to permit liquid body exudates to readily penetrate through its thickness to the absorbent structure 50. The bodyside liner 48 may comprise a variety of suitable materials including, for example and without limitation, porous foams, reticulated foams, apertured plastic films, woven and nonwoven webs, and combinations thereof. The bodyside liner 48 may also be stretchable, and more suitably it may be elastomeric. Suitable elastomeric materials for construction of the bodyside liner 48 are described in U.S. patent application Ser. No. 14/170,077 filed Feb. 3, 2014 by Ruman et al., which is hereby incorporated by reference.

The absorbent structure 50 is suitably compressible, conformable, non-irritating to a wearer's skin, and capable of absorbing and retaining liquids and certain body wastes. For example, the absorbent structure 50 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The absorbent structure 50 may be stretchable so as not to inhibit the stretchability of other components to which the absorbent structure may be adhered, such as the backsheet 46 and bodyside liner 48. After being formed or cut to a desired shape, the absorbent structure 50 may be wrapped or encompassed by a suitable wrap (not shown) that aids in maintaining the integrity and shape of the absorbent structure.

The absorbent assembly 36 may also include a surge management layer (not shown) located adjacent the absorbent structure 50 (e.g., between the absorbent structure 50 and the liner 48) to decelerate and diffuse surges or gushes of liquid that may be rapidly introduced into the absorbent structure 50 of the training pant 20 by the wearer. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, I I et al., the disclosures of which are hereby incorporated by reference.

As illustrated in FIG. 1, the front waist region 22 of the training pant 20 can be selectively joined to the back waist region 24 via a pair of refastenable side seams 70 (one side seam being shown in a fastened configuration and the other side seam being shown in an unfastened configuration) to define a pull-on, pant-like configuration of the training pant having a waist opening, indicated at 66, and two leg openings, indicated at 68. The illustrated refastening seams 70 are defined by first fastening components 90 (e.g., a loop-type fastener) selectively engageable with second fastening components 92 (e.g., hook-type fasteners). The fastening components 90, 92 may include any suitable complementary refastenable fasteners including, for example and without limitation, hook- and loop-type fasteners, other types of mechanical fasteners, adhesive fasteners, cohesive fasteners, and combinations thereof. In some suitable embodiments, the fastening components 90, 92 may be pre-fastened during the manufacturing process of the training pant 20 such that the training pant 20 is supplied to the user in a fastened configuration. While FIG. 1 illustrates the front and back regions 22, 24 being joined together via refastenable seams 70, it is understood that the front and back regions can be joined together via non-refastenable, bonded seams (e.g., by adhesive bonding, ultrasonic bonding, pressure bonding, thermal bonding).

With reference still to FIGS. 1 and 2, the illustrated training pant 20 also includes front and rear waist elastic members 94 configured to form a gasket around the waist opening 66. The waist elastic members 94 can be formed of any suitable elastic material including, for example and without limitation, sheets, strands or ribbons of natural rubber, synthetic rubber, or thermoplastic elastomeric polymers. Other suitable elastic materials from which the waist elastic members 94 can be formed, and suitable methods of incorporating waist elastic members into an absorbent article are described in U.S. patent application Ser. No. 14/068,918 filed Oct. 31, 2013 by Sina et al., and U.S. patent application Ser. No. 14/068,913 filed Oct. 31, 2013 by Bennett et al., the disclosures of which are hereby incorporated by reference.

The illustrated training pant 20 also includes leg elastic members 82 disposed proximate the side edges 28 to create a gasket and to reduce or inhibit leakage of body exudates around the leg openings 68. The leg elastic members 82 can be formed from a variety of suitable elastic materials including, for example and without limitation, sheets, strands or ribbons of natural rubber, synthetic rubber, or thermoplastic elastomeric polymers. The illustrated leg elastic members 82 include at least one elastic element (e.g., an elastic strand 83) adhered to a carrier sheet 84. The leg elastic members 82 can be cut and formed from a continuous ribbon of elastic material, and applied to the training pant 20 as a discrete segment utilizing the apparatus and methods described in more detail herein.

Particular examples of suitable elastic materials for leg elastic members 82 include, without limitation, dry-spun coalesced multifilament spandex elastomeric threads sold under the trade name LYCRA® and available from Invista of Wichita, Kans., U.S.A., vertical filament laminate (VFL) materials, an example of which is described in U.S. Pat. No. 6,916,750 to Thomas et al., which is hereby incorporated by reference; elastic nonwoven composites having an apertured elastic film laminated to one or more nonwoven web materials, examples of which are described in U.S. Pat. No. 7,803,244 issued Sep. 28, 2010 to Siqueira et al., and U.S. Pat. No. 8,361,913 issued Jan. 29, 2013 to Siqueira et al., both of which are hereby incorporated by reference; and other elastic laminates such as single- and dual-faced spandex laminates, stretch-bonded laminates (SBL), and continuous filament stretch-bonded laminates (CFSBL), examples of which are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are hereby incorporated by reference.

In the illustrated embodiment, the leg elastic members 82 are attached to the body-facing side 23 of the chassis 34, and are interposed between the chassis 34 and the absorbent assembly 36. In other suitable embodiments, the leg elastic members 82 may be attached to a body-facing side of the absorbent assembly 36 in addition to the body-facing side 23 of the chassis 34 such that the absorbent assembly 36 is interposed between the leg elastic members 82 and the chassis 34. In yet other suitable embodiments, it is contemplated that the leg elastic members 82 can be attached to the garment-facing side 25 of the chassis 34 in addition to or instead of the leg elastic members 82 attached to the body-facing side 23. That is, in one suitable embodiment, leg elastic members 82 can be attached to both the body-facing and garment-facing sides 23, 25 of the chassis 34. In another suitable embodiment, the leg elastic members 82 can be attached to either the body-facing side 23 or the garment-facing side 25 of the chassis 34.

As shown in FIG. 2, the leg elastic members 82 of the illustrated embodiment are profiled and, more specifically, curved, to provide a more formfitting, comfortable gasket around the leg openings 68 of the training pant 20. In particular, the leg elastic members 82 are highly shaped to provide improved leakage protection and a more appealing aesthetic appearance. More specifically, at least a portion of each leg elastic member 82 has a radius of curvature R1 of less than about 5.0 inches, and more suitably less than about 3.5 inches, along at least a portion of its length, and an amplitude or displacement of between about 2.0 inches and about 8.0 inches, and more suitably between about 3.0 inches and about 8.0 inches. The term "amplitude" as used with reference to the leg elastic members 82 refers to the maximum transverse distance 88 between one of the leg elastic elements and a reference line 89 that intersects both ends of the leg elastic element 82.

FIGS. 3-6 illustrate one suitable embodiment of a shaping device (broadly, an apparatus), indicated generally at 100, for shaping a segment 101 of material into a desired shape, such as the leg elastic members 82 illustrated in FIGS. 1 and 2. The segment 101 of material is shown in broken lines in FIGS. 4 and 6 to illustrate underlying features of the shaping device 100.

As shown in FIGS. 3-6, the illustrated shaping device 100 includes a male forming member 102, a conforming member 104, a female forming member 106, and a drive mechanism 108. The male forming member 102 has a top (as viewed in FIG. 3) or first side 110, a bottom or second side 112 (FIG. 5), a curved sidewall 114 extending between the top and bottom sides 110, 112, and a straight backwall 115 extending between the top and bottom sides 110, 112. The curved sidewall 114 is shaped complementary to the desired shape of the segment 101 of material, which, in the illustrated embodiment, is the shape of the leg elastic members 82 (FIGS. 1 and 2). The curved sidewall 114 of the male forming member 102 is adapted for selective engagement with the conforming member 104. In the illustrated embodiment, the male forming member 102 is operatively connected to the drive mechanism 108 for movement from a first position (FIG. 4) to a second position (FIG. 6) to engage the conforming member 104.

The conforming member 104 has an applicator side 116 for receiving the segment 101 of material thereon, a first engagement side 118 disposed for engagement with the male forming member 102, and a second engagement side 120 disposed for engagement with the female forming member 106. The conforming member 104 includes a plurality of attachment regions 122 disposed on the applicator side 116. Each attachment region 122 is adapted to hold at least a portion of the segment 101 of material on the applicator side 116 of the conforming member 104, as described in more detail herein.

The female forming member 106 includes a curved side 124 shaped complementary to the curved sidewall 114 of the male forming member 102. The female forming member 106 is configured to engage the second engagement side 120 of the conforming member 104 to guide the conforming member 104 into a desired shape when the male forming member 102 engages the conforming member 104. In the illustrated embodiment, the female forming member 106 comprises a first guide 126 and a second guide 128. The first guide 126 is shaped complementary to a first portion of the curved sidewall 114 of the male forming member 102, and the second guide 128 is shaped complementary to a second portion of the curved sidewall 114 of the male forming member 102. The first guide 126 and the second guide 128 cooperatively define the curved side 124 of the female forming member 106.

The drive mechanism 108 is configured to move at least one of the male forming member 102 and the female forming member 106 relative to the conforming member 104 to engage the conforming member 104 between the male forming member 102 and the female forming member 106. In the illustrated embodiment, the drive mechanism 108 is operatively connected to the male forming member 102 along the backwall 115, and is configured to move the male forming from a first position (shown in FIGS. 3-5), in which the male forming member 102 is spaced from the conforming member, and a second position (shown in FIG. 6), in which the male forming member 102 engages the conforming member 104. In the illustrated embodiment, the drive mechanism 108 comprises a pneumatically-actuated cylinder, although it is understood that the drive mechanism 108 may include any suitable device that enables the drive mechanism 108 to function as described herein including, for example and without limitation, a rotating cam or a motorized linear actuator.

Figure 3:
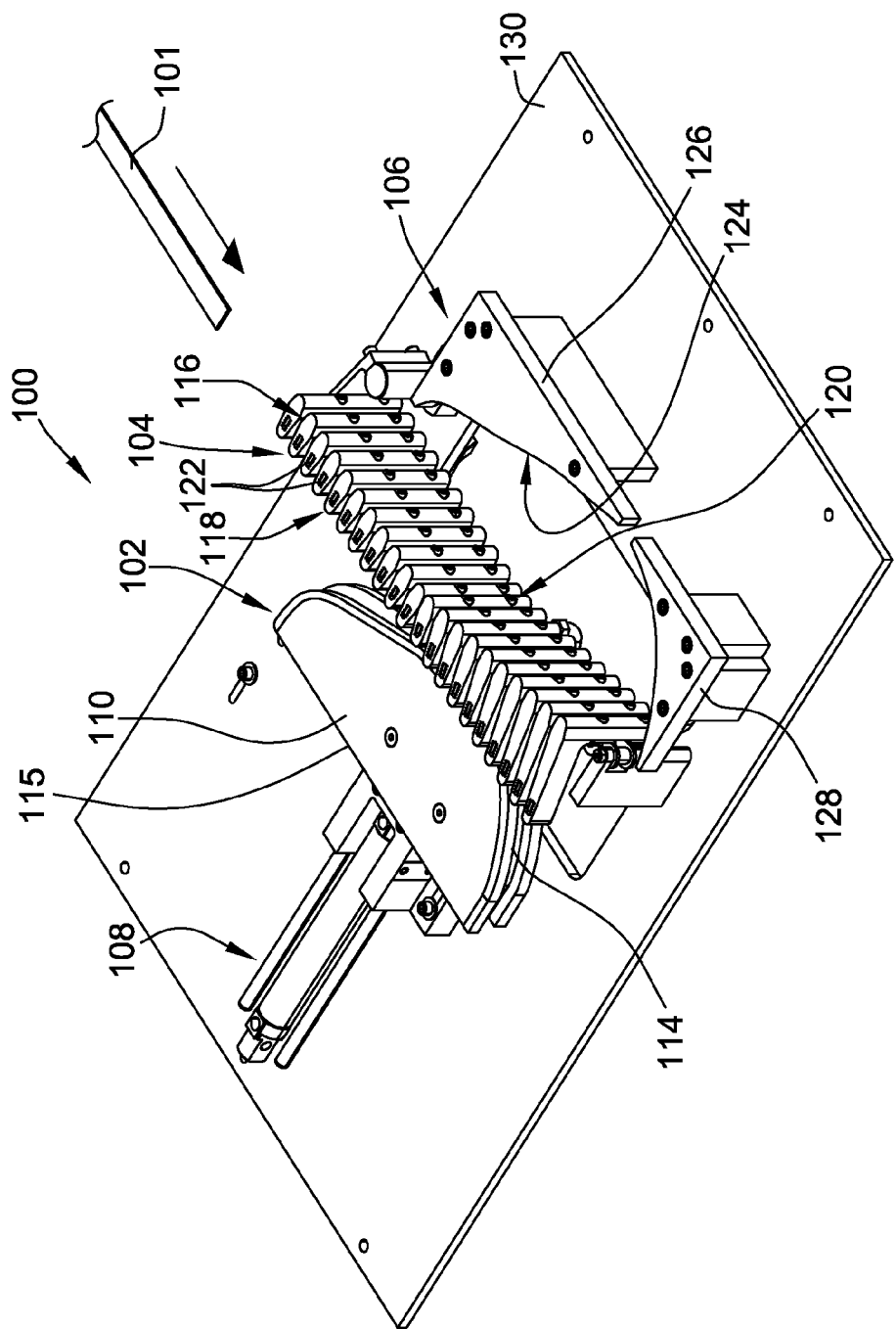
FIG. 3 is a perspective of one suitable embodiment of a shaping device for shaping a segment of material, the shaping device including a forming member and a conforming member.

In the illustrated embodiment, the shaping device 100 is mounted to a mounting surface 130 (FIG. 3). That is, each of the male forming member 102, the conforming member 104, the female forming member 106, and the drive mechanism 108 are connected, directly or indirectly, to the mounting surface 130. The mounting surface 130 may be part of a drum or other rotating device (not shown in FIG. 3) used to apply the segment 101 of material to a moving web after the segment 101 has been shaped to a desired shape. In the illustrated embodiment, the male forming member 102 is movably connected to the mounting surface 130 via the drive mechanism 108, and the female forming member 106 is fixedly mounted to the mounting surface 130. Opposite ends of the conforming member 104 are mounted to the mounting surface, and the conforming member 104 is configured to conform to the shape of the male forming member 102, as described in more detail herein.

As seen in FIGS. 3-6, the illustrated conforming member 104 comprises a chain 132, a tensioning member 134, and a plurality of fingers 136 connected to the chain 132. The illustrated conforming member 104 includes twenty-one fingers, although it is understood that the conforming member 104 may include any suitable number of fingers. The chain 132 includes a first, fixed end 138 and a second end 140 distal from the first end 138. The first end 138 of the chain 132 is rotatably connected to a fixed support 142 by a suitable fastener (e.g., a bolt or pin), and the second end 140 of the chain 132 is pivotally connected to the tensioning member 134 by a suitable fastener (e.g., a bolt or pin). The fixed support 142 and the tensioning member 134 are mounted to the mounting surface 130 (FIG. 3). The tensioning member 134 is configured to maintain tension in the chain 132, and return the conforming member 104 to an initial, non-deformed state (shown in FIGS. 3-5) in the absence of an applied force from the male forming member 102 and/or the female forming member 106. In the illustrated embodiment, the tensioning member 134 comprises a spring loaded pivoting arm 144 having a first end 146 connected to the second end 140 of the chain 132, and a second end 148 connected to a bearing sleeve 150. The bearing sleeve 150 is rotationally biased by a biasing member (not shown) such that the pivoting arm 144 imparts a tensile force to the chain 132. It is contemplated that the tensioning member 134 may include other suitable tensioning devices including, for example and without limitation, a torsion spring, an elastomeric polymer, rubber, an air cylinder, gas spring, or hydraulic arm connected to the conforming member 104 under compression, tension, or torsion with suitable linking mechanisms, and combinations thereof.

In the illustrated embodiment, the conforming member 104 is connected to the male forming member 102 by a linking arm 152 (FIGS. 4 and 5) to impart a desired shape profile to the conforming member 104 when the conforming member 104 is not engaged by the male forming member 102 or the female forming member 106. In particular, the linking arm 152 is pivotally connected to the chain 132 approximately midway between the first end 138 of the chain 132 and the second end 140 of the chain 132, and is pivotally connected to the male forming member 102. The linking arm 152 is configured such that, when the male forming member 102 is in the first position (shown in FIGS. 3-5), the linking arm 152 imparts a force on the chain 132, causing the chain 132 to be at an angled or bent configuration and causing the attachment regions 122 to be aligned in a substantially straight line. It is understood that the linking arm 152 can be connected to the chain 132 at any suitable location to obtain a desired shape profile of the conforming member 104 when the conforming member is not engaged by the male forming member 102 or the female forming member 106. It is also understood that the linking member 152 may be omitted from the shaping device 100.

Figure 6:
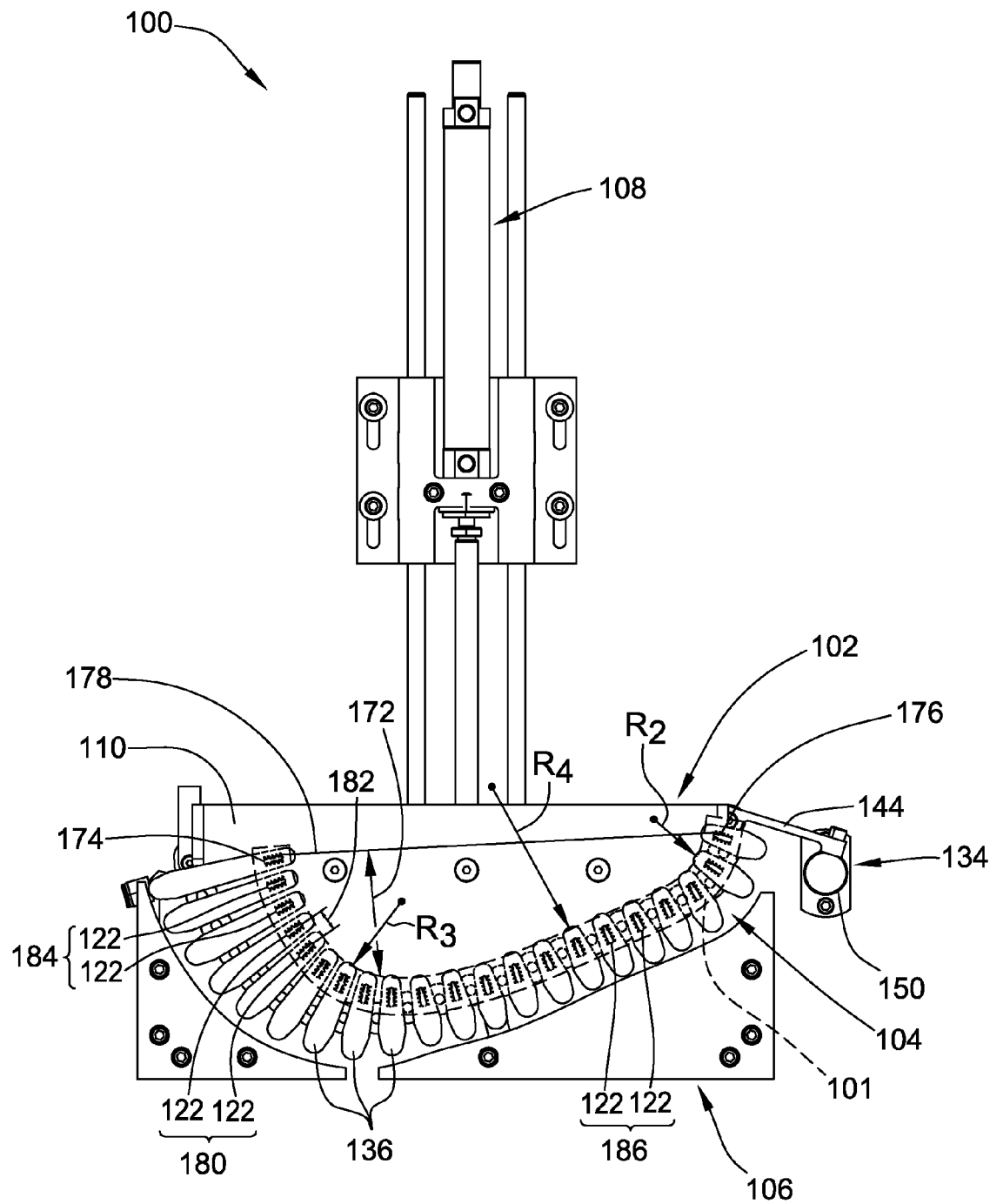
FIG. 6 is a top view of the shaping device of FIG. 4, illustrating the attachment regions of the conforming member in a second shape profile.
Figure 7:
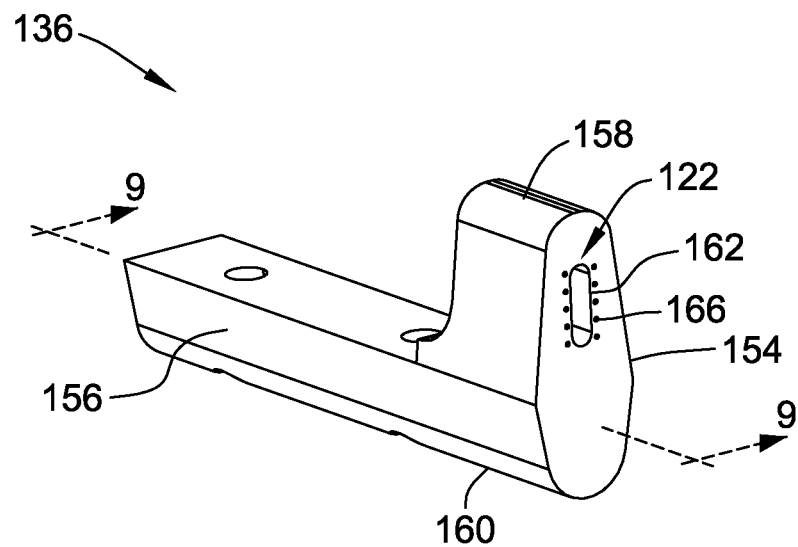
FIG. 7 is an enlarged perspective of one of a plurality of fingers of the conforming member of FIG. 3 removed from the conforming member.
Figure 8:
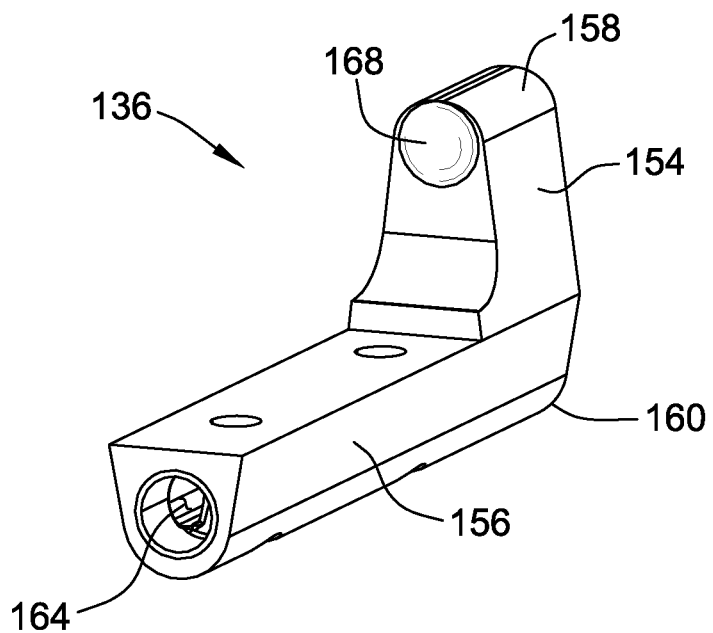
FIG. 8 is another perspective of the finger removed from the conforming member.

FIGS. 7 and 8 are perspective views of one of the fingers 136 of the conforming member 104 shown in FIGS. 3-6, and FIG. 9 is a cross-section of the finger 136 taken along line "9-9" in FIG. 7. Each finger 136 of the conforming member 104 has substantially the same construction as the finger 136 shown in FIGS. 7-9, except some fingers 136 have different dimensions than the finger 136 shown in FIGS. 7-9.

Figure 4:
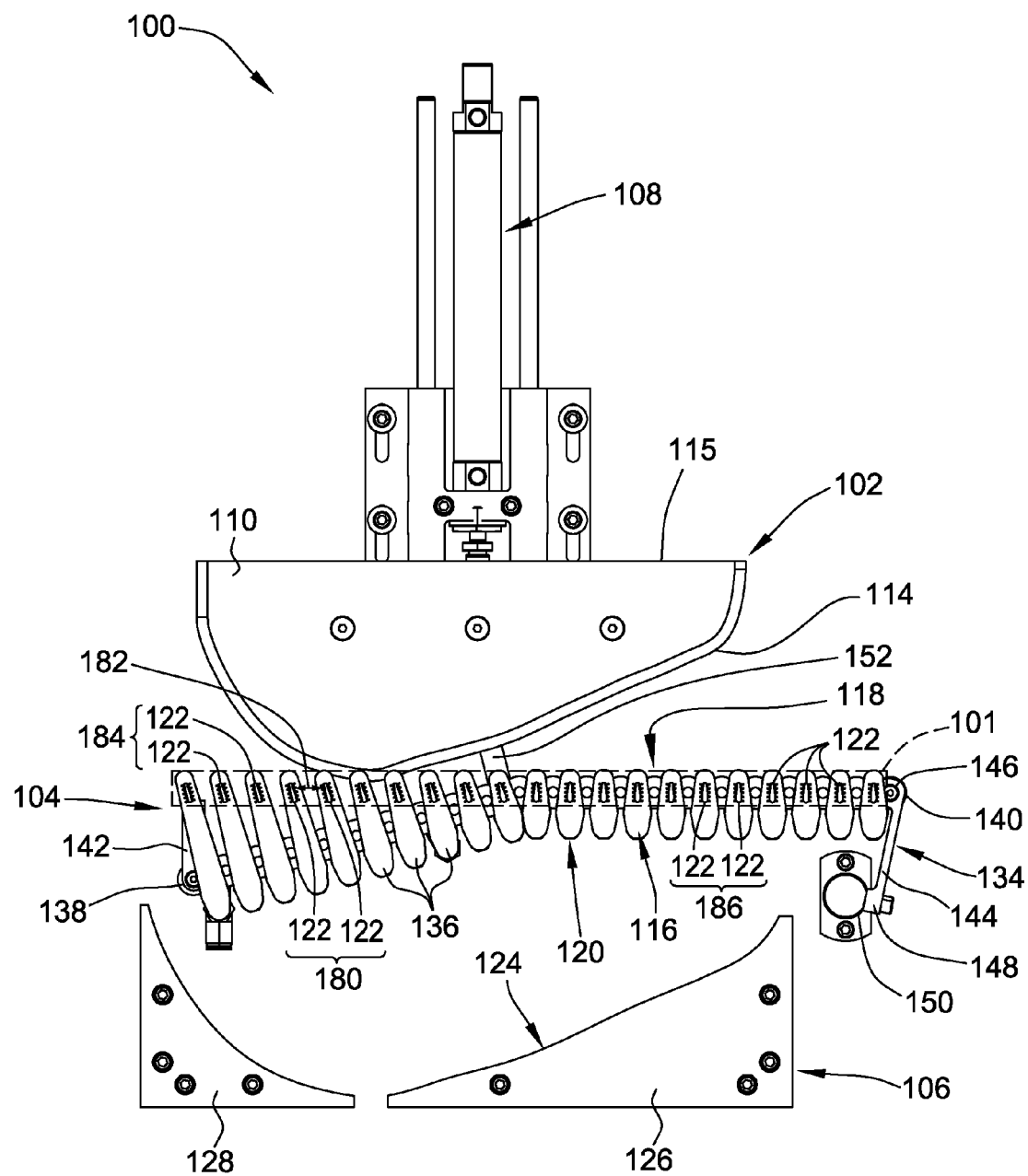
FIG. 4 is a top plan view of the shaping device of FIG. 3, illustrating a plurality of attachment regions of the conforming member in a first shape profile.
Figure 5:
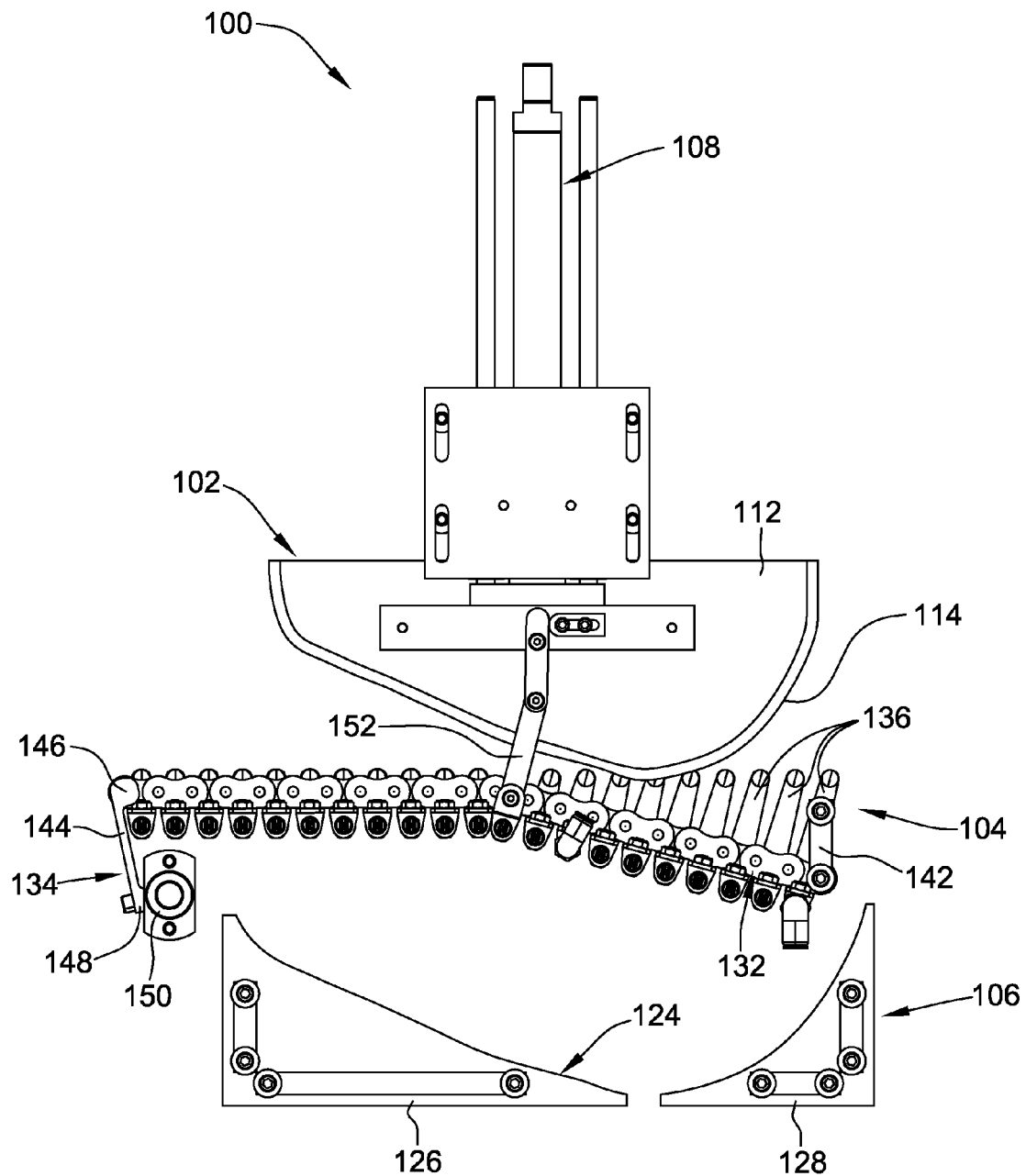
FIG. 5 is a bottom plan view of the shaping device of FIG. 3 illustrating a plurality of chain pieces and associated linkage used to influence the shape of the conforming member.
Figure 9:
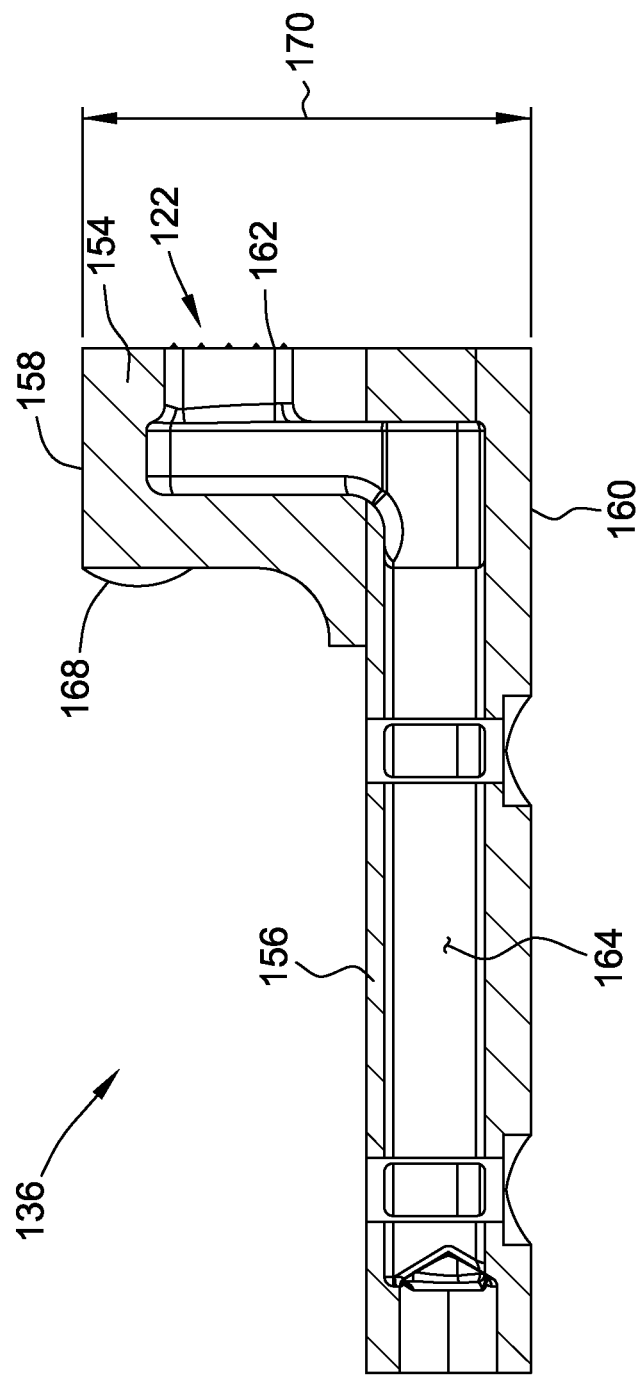
FIG. 9 is a cross-section of the finger shown in FIG. 9 taken along line "9-9" in FIG. 7, the cross-section view being normal to the plane of the cross-section.

As shown in FIGS. 7-9, the finger 136 includes an applicator portion 154 and an engagement portion 156 disposed for direct engagement with the male forming member 102 and the female forming member 106. The applicator portion 154 has a first end 158 and a second end 160 spaced from the first end 158. The engagement portion 156 extends outward from the second end 160 of the applicator portion 154. In the illustrated embodiment, the engagement portion 156 is oriented substantially perpendicular to the applicator portion 154, although it is understood that the engagement portion 156 may be oriented at an angle other than perpendicular to the applicator portion 154. Each finger 136 is connected to the chain 132 along its engagement portion 156 by one or more suitable fasteners (e.g., screws). As shown in FIG. 4, the fingers 136 are arranged along the chain 132 in spaced relation to one another.

Each of the illustrated fingers 136 further includes one of the attachment regions 122 disposed along the applicator portion 154. In the illustrated embodiment, the attachment region 122 is disposed proximate the first end 158 of the applicator portion 154. That is, the attachment region 122 is disposed closer to the first end 158 of the applicator portion 154 than the second end 160. As shown in FIG. 4, the attachment region 122 on each finger 136 is located approximately the same distance from the corresponding first end 158 of each finger 136. In other suitable embodiments, one or more of the fingers 136 may include more than one attachment region 122. In yet other suitable embodiments, one or more of the fingers 136 may not include any attachment regions 122.

In the illustrated embodiment, each attachment region 122 comprises a port 162 operably connected to a vacuum source (such as, e.g., a vacuum pump, a vacuum chamber, etc., not shown) capable of selectively applying a vacuum pressure (i.e., negative pressure) through the port 162 such that the segment 101 of material is generally drawn to and secured against the applicator side 116 of the conforming member 104. The finger 136 defines a vacuum chamber or channel 164 providing fluid communication between the port 162 and the vacuum source. In other words, each port 162 is connected to the vacuum source via the respective vacuum chamber 164. As a result, vacuum may be selectively applied to different attachment regions 122 to selectively hold or release the segment 101 of material at different attachment regions 122 along the conforming member 104. In other suitable embodiments, the attachment regions 122 may be connected to a vacuum source by a common vacuum chamber defined within the conforming member 104. In one suitable embodiment, for example, the conforming member 104 comprises a unitary resilient body (see, e.g., FIG. 10), and has a vacuum chamber providing fluid communication between multiple ports and a vacuum source.

In the illustrated embodiment, the attachment regions 122 further comprise a textured surface 166 configured to hold the segment 101 of material on the conforming member 104. In other embodiments, the attachment regions 122 may comprise only one of the port 162 and the textured surface 166. Other nonslip, textured surfaces suitable for use with the attachment regions 122 include, for example and without limitation, an outwardly perforated metal surface (e.g., perforated stainless steel).

In the illustrated embodiment, the finger 136 further comprises a protrusion 168 extending transversely outward from the applicator portion 154 proximate the first end 158 of the applicator portion 154. The protrusion 168 extends transversely outward from the applicator portion 154 in the same direction as the engagement portion 156, and is configured to engage the top side 110 of the male forming member 102 when the segment 101 of material is applied to a moving web. The male forming member 102 thereby provides a back stop or support for the conforming member 104 when the segment 101 of material is applied to a moving web. The protrusion 168 is hemispherically shaped in the illustrated embodiment, although it is understood that the protrusion may have any suitable shape that allows the conforming member 104 to function as described herein.

As shown in FIG. 9, the applicator portion 154 of the finger 136 extends a length 170 from the first end 158 to the second end 160. As shown in FIG. 4, the length of the fingers 136 varies across the conforming member 104. In particular, beginning with one of the fingers 136 located approximately centrally in the plurality of fingers 136, the length of each finger 136 gradually increases as the distance between the finger 136 and the first end 138 of the chain 132 decreases. Further, each finger 136 located between the centrally located finger 136 and the second end 140 of the chain 132 has substantially the same length.

Referring again to FIGS. 4 and 6, the conforming member 104 is configured to conform to the shape of the male forming member 102, and move between a first configuration and a second configuration to impart a desired shape to the segment 101 of material. FIG. 4 shows the conforming member 104 in a first configuration in which the attachment regions 122 are arranged in a first shape profile. As shown in FIG. 4, the attachment regions 122 are aligned in a substantially straight line when in the first shape profile. In other words, the first shape profile is a substantially straight line to create a straight line infeed for the segment 101 of material.

As shown in FIG. 6, engagement of the conforming member 104 with the male forming member 102 causes the conforming member 104 to conform to the shape of the male forming member 102, in particular the curved sidewall 114 of the male forming member 102, and causes the attachment regions 122 to move from the first shape profile to a second shape profile. The second shape profile is the desired shape of the segment 101 of material.

In the illustrated embodiment, as the male forming member 102 engages each finger 136, the fingers 136 are displaced and cause the chain 132 to conform to the shape of the male forming member 102. As the chain 132 conforms to the shape of the male forming member 102, links of the chain 132 rotate relative to one another, and cause corresponding fingers 136 to move and rotate with the respective chain link to which they are attached. The attachment regions 122 move and rotate with the respective fingers 136 on which they are disposed, resulting in the second shape profile.

As shown in FIG. 6, when the plurality of attachment regions 122 is in the second shape profile, the plurality of attachment regions 122 defines an amplitude 172. More specifically, the plurality of attachment regions 122 includes a first end attachment region, indicated at 174, and a second end attachment region, indicated at 176. The first and second end attachment regions 174, 176 define a reference line 178 that intersects the first and second end attachment regions 174, 176. The amplitude 172 is the maximum transverse distance between the reference line 178 and the shape profile defined by the plurality of attachment regions 122. In the illustrated embodiment, the maximum transverse distance between the reference line 178 and at least one of the attachment regions 122 (i.e., the amplitude 172) is between about 2.0 inches and about 8.0 inches, and more specifically between about 3.0 inches and about 8.0 inches when the attachment regions 122 are in the second shape profile.

Additionally, when the plurality of attachment regions 122 is in the second shape profile, the plurality of attachment regions 122 defines at least one radius of curvature. In the illustrated embodiment, the plurality of attachment regions 122 has at least three different portions each defining a different radius of curvature, indicated at R2, R3, and R4, respectively, in FIG. 6. More specifically, a first portion of the plurality of attachment regions 122 proximate the second end attachment region 176 defines the radius of curvature R2, a second portion of the plurality of attachment regions 122 proximate the first end attachment region 174 defines the radius of curvature R3, and a third portion of the plurality of attachment regions 122 between the first and second portions defines a radius of curvature R4. In the illustrated embodiment, the radius of curvature R2 is the sharpest (i.e., smallest) radius of curvature, and the radius of curvature R4 is the largest radius of curvature. In one suitable embodiment, at least one of the radiuses of curvature R2, R3, and R4 is less than about 5.0 inches, and more suitably less than about 3.5 inches. In the illustrated embodiment, the second shape profile corresponds to the shape of the leg elastic members 82 illustrated in FIG. 2. Thus, each leg elastic member 82 similarly defines three different radiuses of curvature, also indicated at R2, R3, and R4, respectively, in FIG. 2.

In use, the segment 101 of material is fed to the conforming member 104 while the attachment regions 122 are in the first shape profile, and held on the conforming member 104 by the attachment regions 122. The segment 101 is shaped into the desired shape by engaging the conforming member 104 with the male forming member 102 while the segment 101 is held by the attachment regions 122 such that the second shape profile of the attachment regions 122 is imparted to the segment 101 of material. The shaping device 100 is thus configured to impart a desired shape to segments of material, such as leg elastic members 82, as seen in FIG. 2.

The shaping device 100 is particularly suitable for imparting a highly shaped profile to segments of material. For example, the illustrated shaping device 100 is capable of shaping the segment 101 of material such that at least a portion of the segment 101 has a radius of curvature R1 (FIG. 2) of less than about 5.0 inches, and more suitably, less than about 3.5 inches. The illustrated shaping device 100 is also capable of shaping the segment 101 of material such that segment 101 has an amplitude 88 (FIG. 2) or displacement of between about 2.0 inches and about 8.0 inches, and more suitably between about 3.0 inches and about 8.0 inches. It is understood that the shaping device 100 may be configured to shape a segment of material to have a radius of curvature R1 less than about 3.5 inches or greater than about 5.0 inches. It is further understood that the shaping device 100 may be configured to shape a segment of material having an amplitude 88 less than about 2.0 inches or greater than about 8.0 inches.

The illustrated shaping device 100 is also configured to impart a stretch profile to the segment 101 of material. In particular, the plurality of attachment regions 122 includes pairs of adjacent attachment regions 122, one pair being indicated at 180 in FIGS. 4 and 6. Each pair 180 of adjacent attachment regions 122 is spaced by a respective distance 182. As shown in FIGS. 4 and 6, the distance 182 between at least one of the pairs 180 of adjacent attachment regions 122 changes when the attachment regions 122 move from the first shape profile to the second shape profile. In the illustrated embodiment, the distance 182 between the identified pair 180 of adjacent attachment regions 122 decreases, resulting in an area of reduced tension along the segment 101 of material. In other suitable embodiments, the shaping device 100 may be configured such that the distance 182 between at least one of the pairs 180 of the adjacent attachment regions 122 increases, resulting in an area of increased tension along the segment 101 of material. The degree to which the distance between pairs 180 of adjacent attachment regions 122 changes can be adjusted, for example, by varying the length of the fingers 136, by varying the shape of the curved sidewall 114 of the male forming member 102, by varying the position of the attachment regions 122 on the finger 136, and combinations thereof.

The change in distance between each pair 180 of adjacent attachment regions 122 may be uniform across the conforming member 104, or, as illustrated in FIGS. 4 and 6, the change in distance may be different for different pairs 180 of adjacent attachment regions 122. For example, the decrease in distance between a first pair of adjacent attachment regions, indicated at 184 in FIGS. 4 and 6, is greater than the decrease in distance between a second pair of adjacent attachment regions, indicated at 186 in FIGS. 4 and 6. As a result, a differential stretch profile is imparted to the segment 101 of material. As noted above, the degree to which the distance between pairs 180 of adjacent attachment regions 122 changes can be adjusted to obtain a desired differential stretch profile. In some embodiments, for example, the distance between at least one pair of adjacent attachment regions 122 may decrease, while the distance between another pair of adjacent attachment regions 122 may increase.

Figure 10:
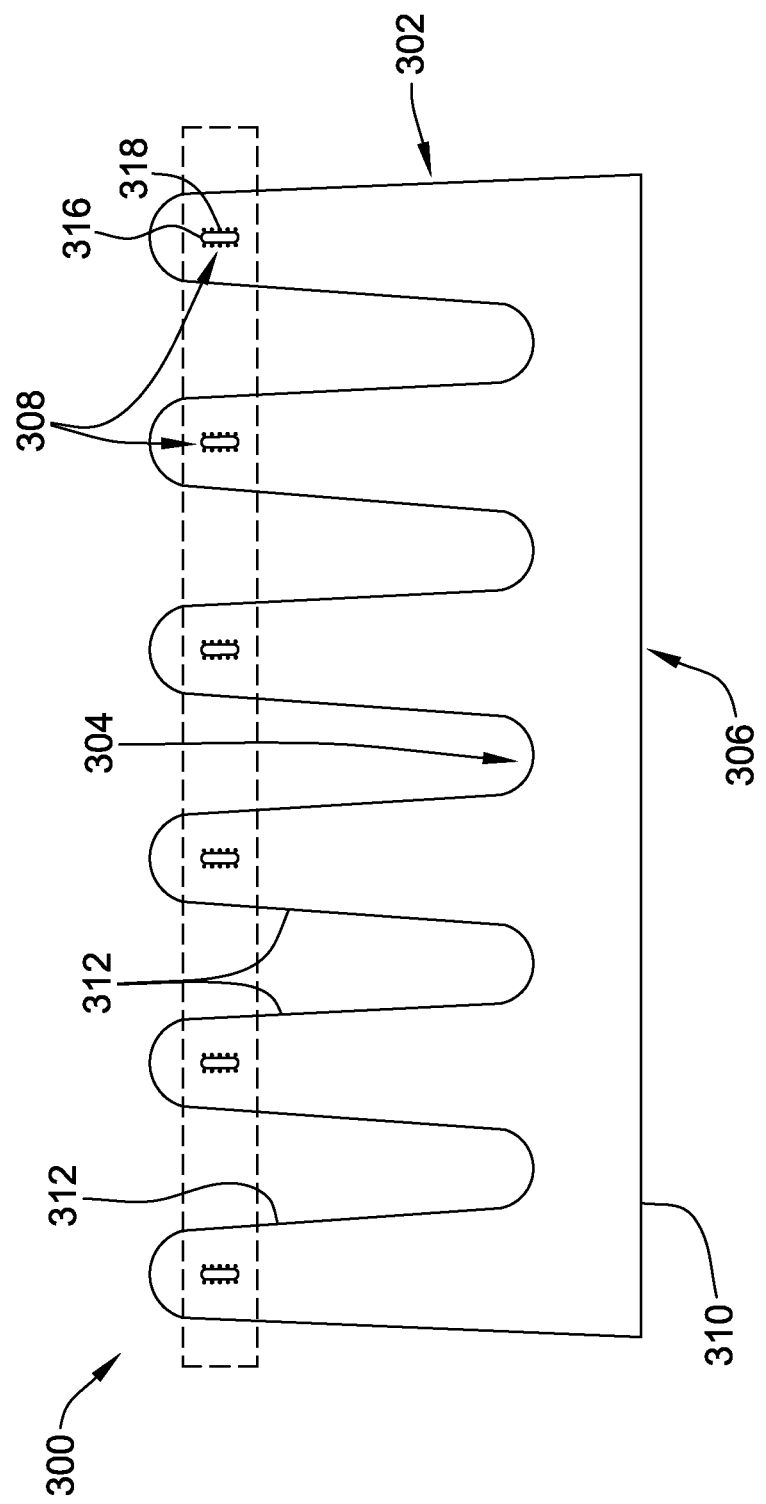
FIG. 10 is a top view of another suitable embodiment of a conforming member suitable for use with the shaping device of FIG. 3, the conforming member including a unitary body.

FIG. 10 is a top view of another suitable embodiment of a conforming member, indicated generally at 300, suitable for use with the shaping device 100 illustrated in FIGS. 3-6. As seen in FIG. 10, the conforming member 300 includes an applicator side 302 for receiving the segment 101 of material thereon, a first engagement side 304 disposed for engagement with the male forming member 102 (FIGS. 3-6), and a second engagement side 306 disposed for engagement with the female forming member 106 (FIGS. 3-6). The conforming member 300 includes a plurality of attachment regions 308 disposed on the applicator side 302, which are identical to and perform the same functions as the attachment regions 122 described above with reference to FIGS. 3-9.

In the embodiment illustrated in FIG. 10, the conforming member 300 comprises a unitary body 310 and a plurality of fingers 312 extending outward from the body 310. The body 310 of the conforming member 300 is suitably constructed from a flexible material such that the conforming member 300 can conform to the shape of the male forming member 102 and the female forming member 106 when compressed between the male forming member 102 and the female forming member 106. In some suitable embodiments, the body 310 of the conforming member 300 is constructed from a resilient flexible material such that the conforming member 300 can return to an initial, non-deformed state (shown in FIG. 10) without the assistance of a separate tensioning member, such as the tensioning member 134 shown in FIGS. 4-6. In other suitable embodiments, the conforming member 300 may include a tensioning member, such as the tensioning member 134 shown in FIGS. 4-6, to maintain tension in the body 310 of the conforming member 300, and to return the conforming member 300 to its initial, non-deformed state (shown in FIG. 10) in the absence of an applied force from the male forming member 102 and/or the female forming member 106 (FIGS. 3-6). Suitable materials from which the body 310 may be constructed include, for example and without limitation, rubber, elastomeric polymers, and combinations thereof.

In the embodiment illustrated in FIG. 10, the fingers 312 are formed integrally with the body 310 of the conforming member 300, and are constructed from the same material as the body 310. In other suitable embodiments, one or more fingers 312 may be formed separately from and attached to the body 310 using suitable fasteners. The illustrated conforming member 300 includes six fingers 312, although it is understood that the conforming member 300 may include any suitable number of fingers that enables the conforming member 300 and the shaping device 100 to function as described herein.

Each of the fingers 312 includes one of the attachment regions 308. In other suitable embodiments, one or more of the fingers 312 may include more than one attachment region 308. In yet other suitable embodiments, one or more of the fingers 312 may not include any attachment regions 308.

As noted above, the attachment regions 308 are identical to and perform the same functions as the attachment regions 122 described above with reference to FIGS. 3-9. Specifically, each attachment region 308 comprises a port 316 operably connected to a vacuum source (such as, e.g., a vacuum pump, a vacuum chamber, etc., not shown) capable of selectively applying a vacuum pressure (i.e., negative pressure) through the port 316 such that the segment 101 of material (FIGS. 3 and 4) is generally drawn to and secured against the applicator side 302 of the conforming member 300.

Each finger 312 defines a vacuum chamber or channel (not shown in FIG. 10) providing fluid communication between the port 316 and the vacuum source. In some suitable embodiments, the vacuum chambers defined by the fingers 312 may be fluidly connected to a single vacuum chamber defined by the unitary body 310, which is fluidly connected to the vacuum source. In other words, all of the vacuum ports 316 may be connected to a single vacuum source via a common vacuum chamber defined by the unitary body 310 of the conforming member 300. In other suitable embodiments, the vacuum ports 316 may be connected to a vacuum source by multiple, separate vacuum chambers defined within the body 310 of the conforming member 300.

As seen in FIG. 10, each attachment region 308 also includes a textured surface 318, which is identical to and performs the same function as the textured surface 166 described above with reference to FIGS. 7-9.

The conforming member 300 performs the same functions as the conforming member 100 described above with reference to FIGS. 3-9. For example, the conforming member 300 is configured to conform to the shape of the male forming member 102 (FIG. 3-6), and move between a first configuration (shown in FIG. 10) and a second configuration to impart a desired shape to the segment 101 of material.

FIG. 10 shows the conforming member 300 in the first configuration in which the attachment regions 122 are arranged in a first shape profile, which is a substantially straight line. Engagement of the conforming member 300 (specifically, the body 310 of the conforming member 300) with the male forming member 102 (FIGS. 3-6) causes the conforming member 300 to conform to the shape of the male forming member 102, in particular the curved sidewall 114 of the male forming member 102, and causes the attachment regions 308 to move from the first shape profile to a second shape profile, which is the desired shape of the segment 101 of material.

FIG. 11 schematically illustrates a portion of a manufacturing process for manufacturing the training pant 20 illustrated in FIGS. 1 and 2, and an apparatus, indicated generally at 200, including a plurality of the shaping devices 100 shown and described above for shaping and applying segments 101 of material to a moving web 201. Although the apparatus 200 is described with reference to the application of a segment of material to a moving web, it is understood that the apparatus 200 may be used to apply segments of a material to an intermittently moving web (i.e., a web that is temporarily stopped while a segment of material is applied).

As shown in FIG. 11, the apparatus 200 includes a rotating device 202 and a plurality of the shaping devices 100 connected to the rotating device 202. Each shaping device 100 is connected to an outer periphery of the rotating device 202, and is oriented such that the applicator side 116 of the conforming member 104 (FIGS. 3 and 4) of each shaping device 100 faces outward and away from the rotating device 202. In the illustrated embodiment, ten shaping devices 100 are connected to the rotating device 202 and are spaced circumferentially around the rotating device 202. It is understood that more or less shaping devices 100 may be connected to the rotating device 202.

As shown in FIG. 11, the apparatus 200 also includes a nip roll 204 disposed on a side of the web 201 opposite the rotating device 202 such that a nip 206 is defined between the nip roll 204 and each shaping device 100, more specifically, between the nip roll 204 and the applicator side 116 of the conforming member 104 (FIGS. 3 and 4) of each shaping device 100.

The apparatus 200 also includes a cutting device 208 configured to sever the segments 101 of material from a ribbon 203 of material. In the illustrated embodiment, the cutting device 208 is a rotary hot knife cutter including at least one blade 210, although it is understood that any suitable cutting device may be used including, for example and without limitation, mechanical pinch type cut-off knives, ultrasonics, or combinations of vacuum rolls or conveyors with cutting devices. In some suitable embodiments, the cutting device 208 may only partially sever the ribbon 203 of material (e.g., using a perforator or perf cutter), and the segment 101 of material may be fully severed from the ribbon 203 by a tensile force applied to the ribbon 203 by rotation of the rotating device 202. In yet other suitable embodiments, the segment 101 of material may be fully severed from the ribbon 203 before being guided to one of the shaping devices 100. In other suitable embodiments, the ribbon 203 may be pre-tensioned before or during the cutting operation to form the discrete segments 101 of material.

During the manufacturing process of the training pant 20, the web 201 of material is fed in a machine direction, indicated by arrow 205. In one suitable embodiment, the web 201 is fed at a high line speed. As used herein, "high line speed" refers to a line speed greater than about 600 feet per minute. Any suitable apparatus may be used to feed the web 201 in the machine direction 205 including, for example and without limitation, nip rolls, tensioning rolls, vacuum conveyors, and combinations thereof. In the illustrated embodiment, the web 201 of material defines the chassis 34 of the training pant 20 (FIGS. 1 and 2), and may be constructed of the same materials as the chassis 34 described above with reference to FIGS. 1 and 2.

Each segment 101 of material is guided to one of the shaping devices 100, in particular, the conforming member 104 of the shaping device 100, to shape the segment 101. In the illustrated embodiment, the segments 101 of material are fed to the rotating device 202 from the ribbon 203 of material. In particular, the ribbon 203 of material is guided to the rotating device 202 and applied to the applicator side 116 of the conforming member 104 (FIGS. 3 and 4) of one of the shaping devices 100. The ribbon 203 of material may be fed to the rotating device by any suitable guiding devices including, for example and without limitation, nip rolls, tensioning rolls, vacuum conveyors, and combinations thereof.

The ribbon 203 of material is held on the conforming member 104 by the attachment regions 122 (FIGS. 3 and 4) as the rotating device 202 rotates in a direction complementary to the machine direction 205, which in FIG. 11 is a counter-clockwise direction. As the rotating device 202 rotates, the cutting device 208 severs the ribbon 203 into one of the segments 101 of material, which is held on the corresponding shaping device 100 by the attachment regions 122. In other suitable embodiments, the segments 101 of material may be guided to the rotating device 202 as discrete segments. That is, the segments 101 of material may be severed from the ribbon 203 prior to being applied to one of the shaping devices 100.

In the illustrated embodiment, the ribbon 203 of material and the segments 101 of material are used to form the leg elastic members 82 of the training pant 20 (FIGS. 1 and 2), and are thus formed from suitable elastic materials. It is understood, however, that the segments 101 of material and the ribbon 203 may be constructed from materials other than elastic materials, and may be used to form components of the training pant 20 other than the leg elastic members 82.

Each segment 101 of material is held on the conforming member 104 (FIGS. 3 and 4) of a corresponding shaping device 100 by the attachment regions 122 of the shaping device 100. In particular, vacuum is applied to the segment 101 of material using the attachment regions 122. The textured surface 166 of the attachment regions 122 (FIG. 7) also holds the segment 101 of material on the conforming member 104. In other suitable embodiments, the segments 101 of material may be held on the conforming member 104 using only one of vacuum and the textured surface 166.

After being applied to one of the shaping devices 100, each segment 101 of material is shaped into a desired shape with the corresponding shaping device 100. Specifically, with additional reference to FIGS. 4 and 6, each segment 101 is shaped by engaging the conforming member 104 of the corresponding shaping device 100 with the male forming member 102 along the first engagement side 118 of the conforming member 104. Each segment 101 of material is shaped into the desired shape while the rotating device 202 rotates, and moves the segment 101 towards the moving web 201.

In some suitable embodiments, each segment 101 of material may be shaped such that at least a portion of each segment 101 has a radius of curvature of less than about 5.0 inches, and more suitably, less than about 3.5 inches. Additionally or alternatively, each segment 101 of material may be shaped such that each segment 101 has an amplitude or displacement of between about 2.0 inches and about 8.0 inches, and more suitably between about 3.0 inches and about 8.0 inches.

The manufacturing process of the training pant 20 may also include imparting a stretch profile to the segments 101 of material. With additional reference to FIGS. 4 and 6, for example, the manufacturing process may include imparting a stretch profile to each segment 101 of material using one of the shaping devices 100 by changing the distance 182 between at least one of the pairs 180 of adjacent attachment regions 122 while the segment 101 is held on the conforming member 104 with the attachment regions 122. In another suitable embodiment, the manufacturing process may include imparting a differential stretch profile to the segment 101 of material by changing the distances between pairs 180 of adjacent attachment regions 122 by different amounts. With additional reference to FIGS. 4 and 6, for example, a differential stretch profile may be imparted to the segment 101 of material by changing the distance between the first pair 184 of adjacent attachment regions 122 by a different amount than the distance between the second pair 186 of adjacent attachment regions 122.

Each segment 101 of material is attached to the moving web 201 after being shaped into a desired shape and/or being stretched with a desired stretch profile with the shaping devices 100. In one suitable embodiment, the segments 101 of material are attached to the web 201 while the web is moving at a high line speed. In the illustrated embodiment, each segment 101 is attached to the web 201 by passing the segment 101 between the nip 206 defined by the nip roll 204 and the applicator side 116 of the conforming member 104 (FIGS. 3 and 4) of each shaping device 100. The segments 101 of material may be applied to the web using any suitable attachment means including, for example and without limitation, adhesives, ultrasonic bonding, thermal bonding, pressure bonding, and combinations thereof. In the illustrated embodiment, each segment 101 is attached adjacent to one of side edges 28 of the training pant 20, although it is understood that the segments 101 can be attached at any suitable location on the web 201.

The shaping devices 100 may be articulated (i.e., rotated or pivoted) when applying the segments 101 of material to the web 201 to maintain substantially flush engagement between the applicator side 116 of the conforming member 104 (FIGS. 3 and 4) and the web 201. The apparatus 200 may include any suitable articulating devices to articulate the shaping devices 100 including, for example and without limitation, camming devices. In one suitable embodiment, for example, each shaping device 100 is pivotally mounted to a cam follower that is moved radially inward and outward by a cam to articulate the shaping device 100. The cam may have any suitable cam profile that enables the apparatus 200 to function as described herein. The shaping devices 100 may be articulated at times other than during application of the segment 101 of material to the web 201 including, for example and without limitation, when the ribbon 203 or one of the segments 101 of material is applied to one of the shaping devices 100. Additionally or alternatively, the web 201 may be fed into and/or out of the nip 206 at an angle to facilitate application of the segment 101 of material to the web 201.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. Apparatus for shaping a segment of material, the apparatus comprising:
    a forming member having a curved sidewall shaped complementary to a desired shape of the segment of material; and
    a conforming member having an applicator side and an engagement side disposed for engagement with the curved sidewall of the forming member, the conforming member comprising a plurality of attachment regions disposed on the applicator side, each attachment region adapted to hold the segment of material on the conforming member,
    wherein engagement of the conforming member with the forming member causes the attachment regions to move from a first shape profile to a second shape profile, the second shape profile being the desired shape of the segment of material.

2. The apparatus as set forth in claim 1, wherein the plurality of attachment regions includes a pair of adjacent attachment regions spaced by a distance in the first shape profile, wherein engagement of the conforming member with the forming member changes the distance between the pair of adjacent attachment regions to impart a stretch profile to the segment of material.

3. The apparatus as set forth in claim 2, wherein the pair of adjacent attachment regions is a first pair, the plurality of attachment regions including a second pair of adjacent attachment regions spaced by a distance in the first shape profile, wherein engagement of the conforming member with the forming member changes the distance between the second pair of adjacent attachment regions by a different amount than the distance between the first pair of adjacent attachment regions to impart a differential stretch profile to the segment of material.

4. The apparatus as set forth in claim 1, wherein the conforming member comprises:
    a chain;
    a tensioning member operatively connected to the chain; and
    a plurality of fingers connected to the chain, each finger having at least one of the attachment regions disposed thereon.

5. The apparatus as set forth in claim 1, wherein each attachment region is defined by a port disposed on the applicator side of the conforming member, each port being in fluid communication with a vacuum source.

6. The apparatus as set forth in claim 1, wherein the forming member is a male forming member, the apparatus further comprising a female forming member shaped complementary to the male forming member, the male forming member configured to press the conforming member between the male forming member and the female forming member.

7. The apparatus as set forth in claim 1, further comprising a drive mechanism operatively connected to the forming member, the drive mechanism configured to move the forming member from a first position to a second position to engage the conforming member.

8. The apparatus as set forth in claim 1, wherein the plurality of attachment regions includes a first end attachment region and a second end attachment region, the first and second end attachment regions defining a reference line that intersects the first and second end attachment regions, wherein a maximum transverse distance between the reference line and at least one of the attachment regions is between about 2.0 inches and about 8.0 inches when the attachment regions are in the second shape profile.

9. The apparatus as set forth in claim 8, wherein the maximum transverse distance is between about 3.0 inches and about 8.0 inches when the attachment regions are in the second shape profile.

10. Apparatus for applying a segment of material to a web, the apparatus comprising:
    a rotating device; and
    a shaping device connected to the rotating device, the shaping device comprising:
        a forming member having a curved sidewall shaped complementary to a desired shape of the segment of material; and
        a conforming member having an applicator side and an engagement side disposed for engagement with the curved sidewall of the forming member, the conforming member comprising a plurality of attachment regions disposed on the applicator side, each attachment region adapted to hold the segment of material on the conforming member,
    wherein engagement of the conforming member with the forming member causes the attachment regions to move from a first shape profile to a second shape profile, the second shape profile being the desired shape of the segment of material.

11. The apparatus as set forth in claim 10, wherein the plurality of attachment regions includes a pair of adjacent attachment regions spaced by a distance in the first shape profile, wherein engagement of the conforming member with the forming member changes the distance between the pair of adjacent attachment regions to impart a stretch profile to the segment of material.

12. The apparatus as set forth in claim 11, wherein the pair of adjacent attachment regions is a first pair, the plurality of attachment regions including a second pair of adjacent attachment regions spaced by a distance in the first shape profile, wherein engagement of the conforming member with the forming member changes the distance between the second pair of adjacent attachment regions by a different amount than the distance between the first pair of adjacent attachment regions to impart a differential stretch profile to the segment of material.

13. The apparatus as set forth in claim 10, wherein the attachment regions are arranged in an arcuate shape when the attachment regions are in the second shape profile.

14. The apparatus as set forth in claim 13, wherein the attachment regions are aligned with one another in a substantially straight line when the attachment regions are in the first shape profile.

15. The apparatus as set forth in claim 10, wherein the rotating device is disposed on a first side of the web, the apparatus further comprising a nip roll disposed on a second side of the web opposite the first side to define a nip between the nip roll and the applicator side of the conforming member.

16. The apparatus as set forth in claim 10, wherein the shaping device is one of a plurality of shaping devices disposed circumferentially on the rotating device.

17. A method of applying a segment of material to a web, the method comprising:
   guiding the segment of material to a conforming member having an engagement side and an applicator side having a plurality of attachment regions;
   holding the segment of material on the conforming member with the attachment regions;
   shaping the segment of material by engaging the conforming member with a forming member along the engagement side of the conforming member to move the attachment regions from a first shape profile to a second shape profile; and
   attaching the segment of material to the web.

18. The method as set forth in claim 17, wherein the plurality of attachment regions includes pairs of adjacent attachment regions, each pair of adjacent attachment regions spaced by a respective distance, the method further comprising imparting a stretch profile to the segment of material by changing a distance between at least one of the pairs of adjacent attachment regions.

19. The method as set forth in claim 17, wherein the plurality of attachment regions includes pairs of adjacent attachment regions, each pair of adjacent attachment regions spaced by a respective distance, the method further comprising imparting a differential stretch profile to the segment of material by changing a first distance between a first pair of adjacent attachment regions by a different amount than a second distance between a second pair of adjacent attachment regions.

20. The method as set forth in claim 17, wherein guiding the segment of material comprises guiding a segment of elastic material to the conforming member.

21. The method as set forth in claim 17, wherein shaping the segment of material includes shaping the segment of material such that at least a portion of the segment of material has a radius of curvature of less than about 5.0 inches.

22. The method as set forth in claim 21, wherein shaping the segment of material includes shaping the segment of material such that at least a portion of the segment of material has a radius of curvature of less than about 3.5 inches.

23. The method as set forth in claim 17, wherein the segment of material includes a first end and a second end, the first and second ends defining a reference line intersecting the first and second ends, wherein shaping the segment of material includes shaping the segment of material such that a maximum transverse distance between the reference line and the segment of material is between about 2.0 inches and about 8.0 inches.

24. The method as set forth in claim 23, wherein shaping the segment of material includes shaping the segment of material such that the maximum transverse distance is between about 3.0 inches and about 8.0 inches.

25. The method as set forth in claim 17, wherein holding the segment of material on the conforming member includes applying a vacuum to the segment of material.

* * * * *